(12) United States Patent
Kolchin et al.

(10) Patent No.: US 9,389,349 B2
(45) Date of Patent: Jul. 12, 2016

(54) SYSTEM AND METHOD TO DETERMINE DEPTH FOR OPTICAL WAFER INSPECTION

(71) Applicant: KLA-Tencor Corporation, Milpitas, CA (US)

(72) Inventors: Pavel Kolchin, Fremont, CA (US); Mikhail Haurylau, San Jose, CA (US); Robert Danen, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 137 days.

(21) Appl. No.: 13/840,329

(22) Filed: Mar. 15, 2013

(65) Prior Publication Data

US 2014/0268117 A1    Sep. 18, 2014

(51) Int. Cl.
*G01N 21/00* (2006.01)
*G02B 5/28* (2006.01)
*G01N 21/95* (2006.01)
*G02B 5/30* (2006.01)

(52) U.S. Cl.
CPC .............. *G02B 5/28* (2013.01); *G01N 21/9505* (2013.01); *G02B 5/3083* (2013.01)

(58) Field of Classification Search
CPC ... G01N 21/88; G01N 21/00; G01N 21/9501; G01C 3/08; G06F 19/00; G02B 5/28; H01L 21/48

See application file for complete search history.

(56) References Cited

U.S. PATENT DOCUMENTS

| | | | | |
|---|---|---|---|---|
| 5,936,726 A | * | 8/1999 | Takeda et al. | 356/237.2 |
| 6,353,222 B1 | | 3/2002 | Dotan | |
| 6,734,960 B1 | * | 5/2004 | Goto et al. | 356/237.1 |
| 2005/0259917 A1 | | 11/2005 | Afonso et al. | |
| 2007/0127041 A1 | | 6/2007 | Dowski, Jr. | |
| 2008/0137059 A1 | * | 6/2008 | Piestun et al. | 356/4.01 |
| 2009/0251690 A1 | * | 10/2009 | Otani et al. | 356/237.3 |
| 2010/0188656 A1 | * | 7/2010 | Matsui et al. | 356/237.3 |
| 2012/0075609 A1 | | 3/2012 | Novak | |
| 2013/0154112 A1 | * | 6/2013 | Zhang et al. | 257/774 |
| 2013/0208269 A1 | * | 8/2013 | Cai et al. | 356/237.5 |
| 2013/0304399 A1 | * | 11/2013 | Chen et al. | 702/40 |

FOREIGN PATENT DOCUMENTS

KR     1020060034391     4/2006

OTHER PUBLICATIONS

Schechner: Yoav Y., Rafael Piestun and Joseph Shamir, "Wave propagation with rotating intesity distributions," Jul. 1996, pp. R50-R53, Physical Review E, vol. 54, No. 1.

Pavani, Sri Rama and Rafael Piestun, "High-efficiency rotating point spread functions," Mar. 3, 2008, pp. 3484-3489. Optics Express vol. 16, No. 5.

(Continued)

*Primary Examiner* — Tarifur Chowdhury
*Assistant Examiner* — Jamil Ahmed
(74) *Attorney, Agent, or Firm* — Simpson & Simpson, PLLC

(57) ABSTRACT

A computer-based method for inspecting a wafer, including: storing, in a memory element for at least one computer, computer readable instructions; detecting a first light beam rotating in a first spiral about a first central axis; and executing, using a processor for the at least one computer, the computer readable instructions to generate, using the detected first light beam, an image including at least one shape, determine an orientation of the at least one shape or a size of the at least one shape, and calculate a depth of a defect in the wafer according to the orientation or the size.

23 Claims, 13 Drawing Sheets

(56) References Cited

OTHER PUBLICATIONS

Greengard Adam, Yoav Y. Schechner and Rafael Peistun. "Depth from diffracted rotation." Optic Letters, Jan. 15, 2006, pp. 181-183 vol. 31, No. 2.

Pavani, Sri Rama Prasanna and Rafael Piestun. "Three dimensional tracking of fluorescent microparticles using a photon-limited double-helix response system." 22 Optics Express, Dec. 2008, pp. 22048-22057, vol. 16, No. 26.

Thompson, M.A. Lew, M.D, M. Badieirostami and W.E. Moerner. "Nano Letters 10, 211-218" Stanford University, Stanford, CA 94305, 2010.

Piestun, Rafael, Yoav Y. Schechner and Joseph Shamir. "Propagation-invariant wave fields with finite energy." Feb. 2000, pp. 294-304. J. Opt. Soc. Am. A/vol. 17, No. 2.

* cited by examiner

SYSTEM AND METHOD TO DETERMINE DEPTH FOR OPTICAL WAFER INSPECTION

TECHNICAL FIELD

The present disclosure relates to a system and method for using a spiral light beam to inspect a semi-conductor wafer, in particular, using the spiral light beam to accurately determine a depth of a defect in a semi-conductor wafer. The present disclosure relates to a system and method for adjusting an auto-focus for a wafer inspection system using a spiral light beam. The present disclosure relates to a phase filter generating a spiral light beam with increased rotational speed.

BACKGROUND

A defect in a semi-conductor wafer can be classified as a defect of interest (DOI), which could impact utility of the wafer, or a nuisance defect, which can be effectively ignored. In general, a defect closer to the surface of a wafer is more likely to be a DOI. As the vertical dimensions of semi-conductor devices increase, for example as in tri-gate transistors and 3-D NAND memories, it becomes increasing important to accurately determine defect depths, in particular, to ascertain whether a defect is near the top/surface of the wafer or deeper in the wafer.

FIG. 12 is a pictorial representation of light intensity used in a prior art method for determining a depth of a defect in a semi-conductor wafer. In FIG. 12 a color scale of intensities 6 (red—lowest intensity) to 20 (purple—greatest intensity) is shown on the right-hand side. It is known to detect a defect in a semi-conductor wafer using optical means. In terms of optical detection, a defect is characterized by having light scatter different from surrounding structure and can be a particle, a gap, or a missing or misshaped pattern. It is known to illuminate a wafer including one or more defects with light free of a spiral wavefront or orbital angular momentum, collect the light scattered and reflected by the wafer, and generate an image. As shown in FIG. 12, the image includes respective areas 800 of varying intensity. A defect is generally identified by an area of differing intensity, and a depth is estimated according to the relative intensity of the area. In FIG. 12, areas 802A-F are associated with defects 130A-F, respectively, described below for FIG. 4. The image is referenced to a focal plane set at a specific distance, for example, as a z position of interest, such as the surface of the wafer. However, it is extremely difficult to differentiate between an intensity associated with a defect at the focal plane and a defect close to the focal plane. Further, the type of defect (size or optical characteristics) can influence the intensity independently of the depth of the defect. For example, a larger defect at a distance from the focal plane can mimic a smaller defect at the focal plane. It is extremely difficult to ascertain how much of a particular intensity is due to the depth of a defect and how much is due to the type of the defect.

SUMMARY

According to aspects illustrated herein, there is provided a computer-based method for inspecting a wafer, including: storing, in a memory element for at least one computer, computer readable instructions; detecting a first light beam rotating in a first spiral about a first central axis; and executing, using a processor for the at least one computer, the computer readable instructions to generate, using the detected first light beam, an image including at least one shape, determine an orientation of the at least one shape or a size of the at least one shape, and calculate a depth of a defect in the wafer according to the orientation or the size.

According to aspects illustrated herein, there is provided a computer-based apparatus for inspecting a wafer, including: at least one computer including a processor and a memory element configured to store computer readable instructions; and a detector arranged to detect a first light beam rotating in a first spiral about a first central axis. The processor is configured to execute the computer readable instructions to: generate, using the detected first light beam, an image including at least one shape; determine an orientation of the at least one shape or a size of the at least one shape; and calculate a depth of a defect in the wafer according to the orientation or the size.

According to aspects illustrated herein, there is provided a computer-based method for adjusting an auto-focus in a wafer inspection system, including: comparing, using an electronic feedback loop system, an intensity of a first light beam rotating in a first spiral about a first central axis; and when the intensity is less than a preselected threshold, adjusting, using a wafer adjustment system, a position of the wafer until the intensity reaches the preselected threshold.

According to aspects illustrated herein, there is provided a computer-based apparatus for adjusting an auto-focus in a wafer inspection system, including: a wafer adjustment system; and an electronic feedback loop system configured to compare an intensity of a first light beam rotating in a first spiral about a first central axis, and when the intensity is less than a preselected threshold, adjust, using the wafer adjustment system, a position of the wafer until the intensity reaches the preselected threshold.

According to aspects illustrated herein, there is provided a phase filter, including: a structure characterized by: a plurality of Gauss-Laguerre Eigen modes, each Gauss-Laguerre Eigen mode including a respective energy number and a respective azimuthal number in a modal plane; and a rotational line passing through the plurality of Gauss-Laguerre Eigen modes in the modal plane and having a slope greater than 2. The modal plane is represented by a graph having energy numbers along a first axis and azimuthal numbers along a second axis orthogonal to the first axis, and a slope of the rotational line is defined by a change in values for the respective energy numbers divided by a change in values for the respective azimuthal numbers.

According to aspects illustrated herein, there is provided a method of forming a phase filter, including optimizing a linear combination of Laguerre polynomials such that the slope of a rotation line in a modal plane is greater than 2.0. The slope of the rotational line is defined by a change in values for respective energy numbers divided by a change in values for respective azimuthal numbers for a plurality of Gauss-Laguerre Eigen modes. The energy numbers form a first axis in a modal plane. The azimuthal numbers form a second axis, orthogonal to the first axis, in the modal plane.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements of the disclosure. It is to be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure.

Figure 1:
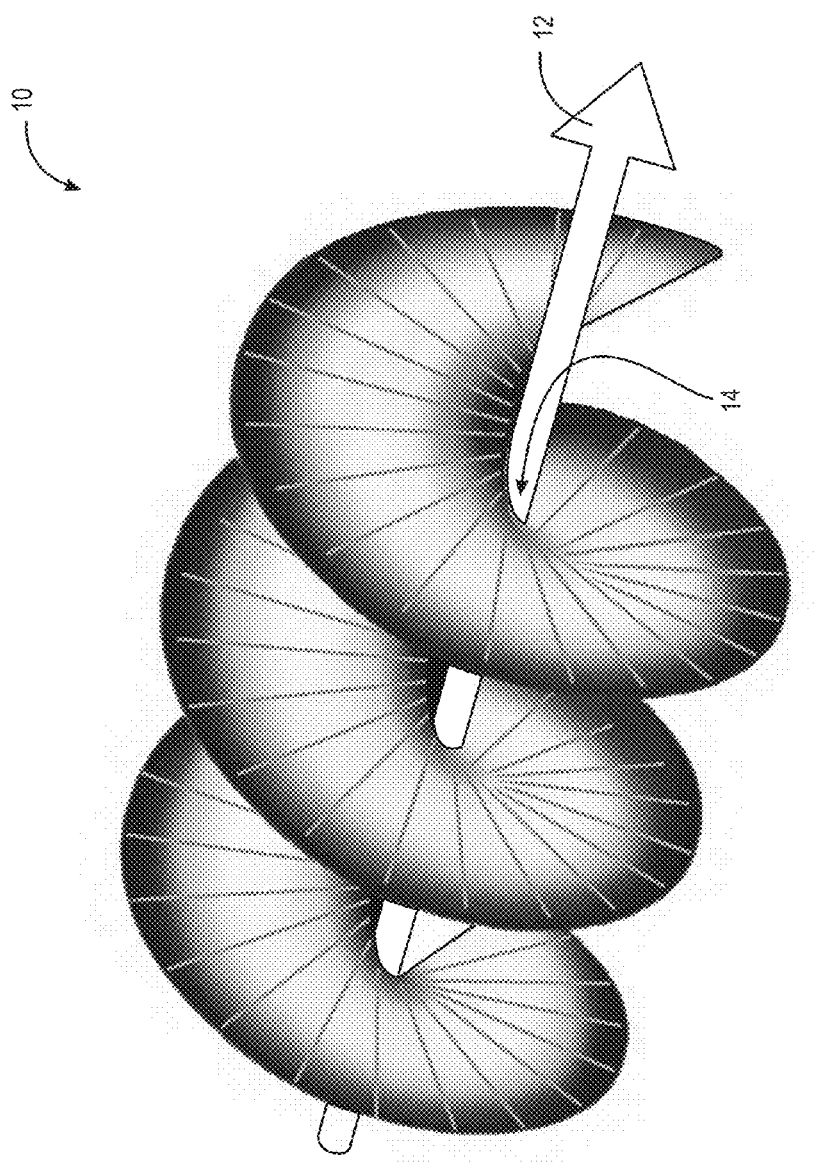
FIG. 1 is a pictorial representation of a spiral light beam.

FIG. 1 is a pictorial representation of light beam 10 rotating in a spiral about beam, or central, axis 12. Light beam 10 has orbital angular velocity and distinctive optical properties and behavior. Orbital angular momentum of light (OAM) is the component of angular momentum of a light beam that is dependent on the field spatial distribution, and not on the polarization. It can be further split into an internal and an external OAM. The internal OAM is an origin-independent angular momentum of a light beam that can be associated with a twisted wavefront. The external OAM is the origin-dependent angular momentum that can be obtained as cross product of the light beam position (center of the beam) and its total linear momentum. Thus, the wavefront of beam 10 is shaped as a spiral, with optical vortex 14 in the center, at beam axis 12, as shown in FIG. 1.

Figure 2:
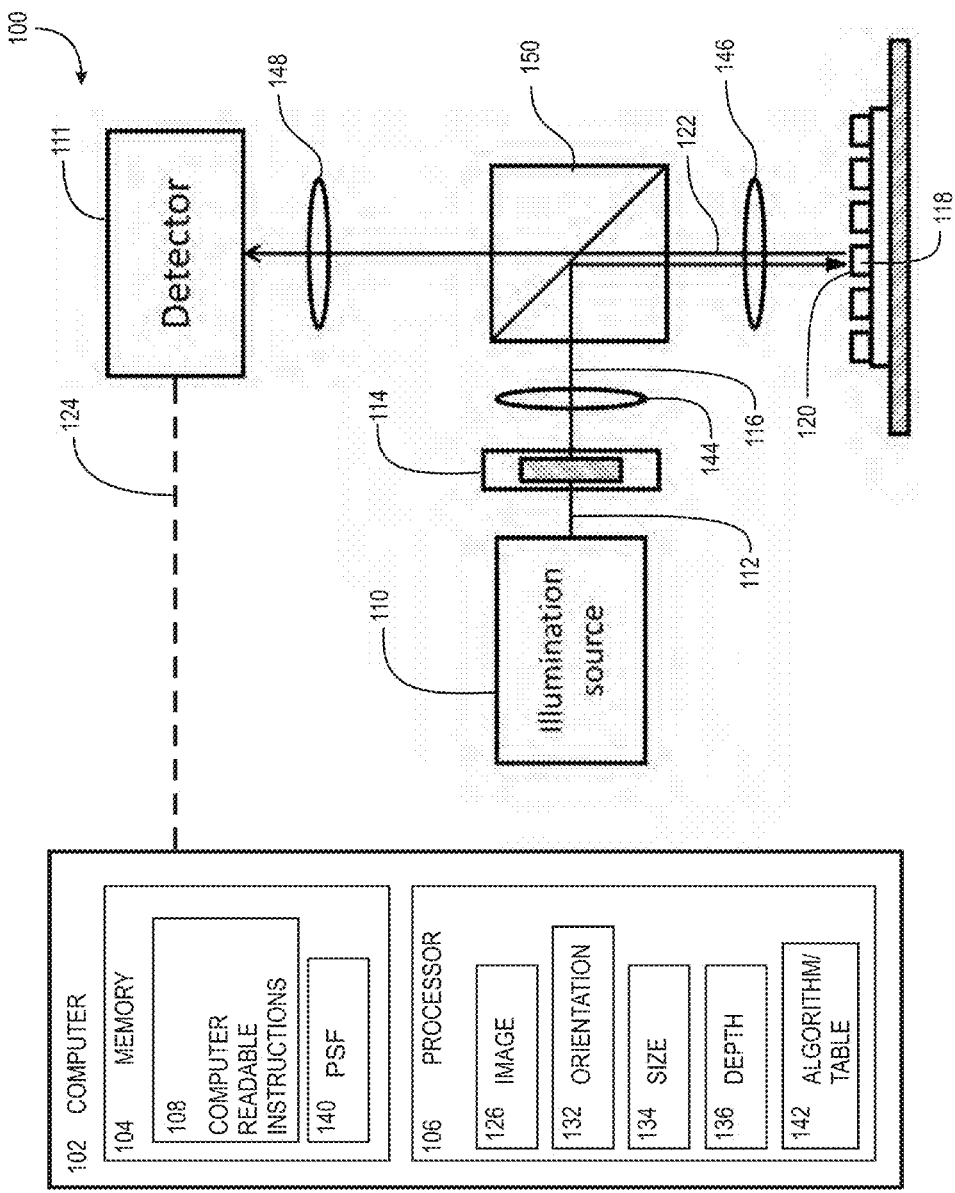
FIG. 2 is schematic representation of a computer-based apparatus for inspecting a semi-conductor wafer using a spiral light beam.

FIG. 2 is schematic block diagram of computer-based apparatus 100 for inspecting a semi-conductor wafer using a spiral light beam.

Figure 2A:
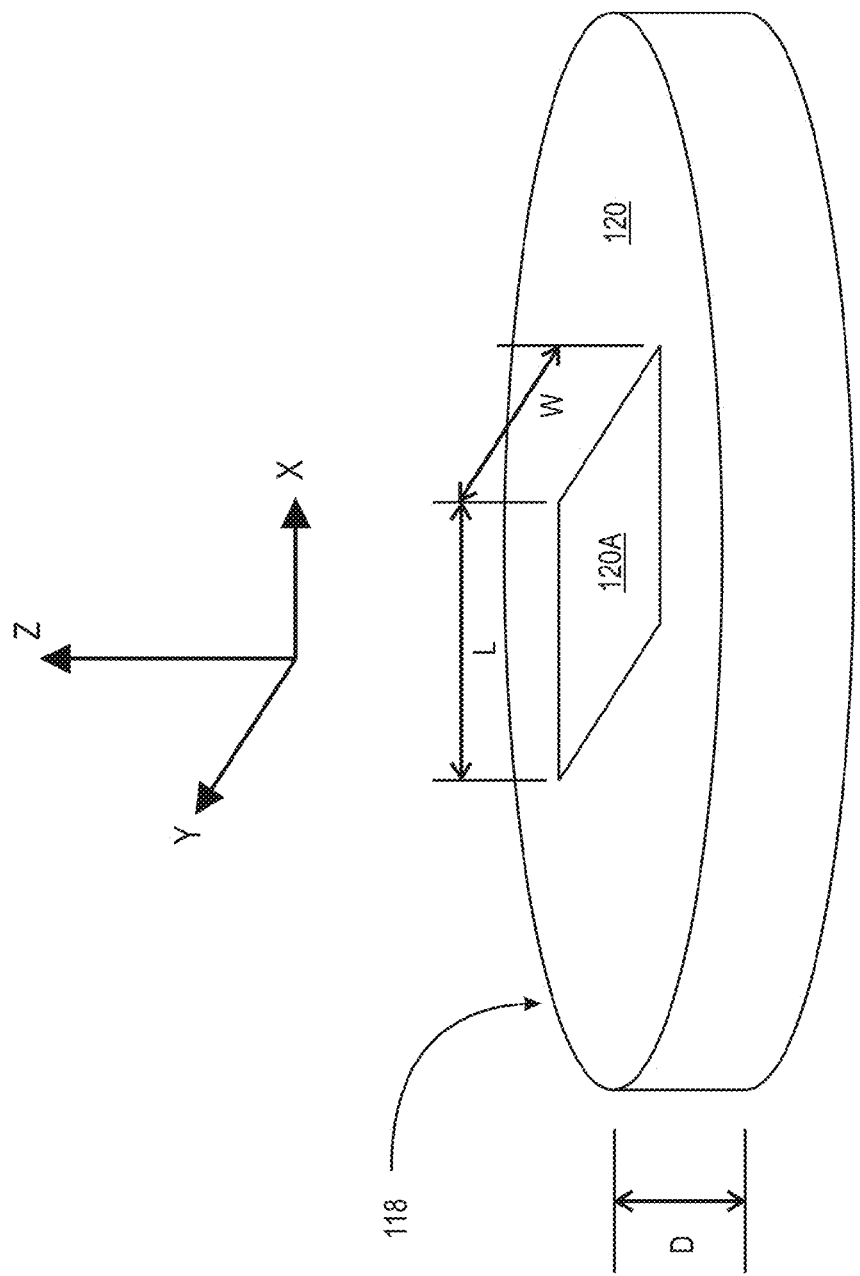
FIG. 2A is a schematic representation of an inspection area in the wafer in FIG. 2.

FIG. 2A is a schematic representation of the wafer in FIG. 2.

The following should be viewed in light of FIGS. 1 through 2A. System 100 includes at least one computer 102 with memory element 104 and processor 106. Memory element 104 is configured to store computer executable instructions 108. System 100 includes light, or illumination, source 110 and detector 111. Light source 110 is arranged to emit light 112 free of a spiral wavefront or orbital angular momentum. Phase filter 114 is arranged to filter light 112 to generate light beam 116, rotating in a spiral about a central axis (for example as shown in FIG. 1) and having orbital angular velocity. Wafer 118 has thickness D in a z direction, orthogonal to x and y directions, and surface 102 including inspection area 120A. Light beam 116 illuminates area 120A having length L in the x direction, width W in the y direction orthogonal to the x direction, and depth D. The wafer can be made of any material known in the art, through which light can be transmitted. In the exemplary discussion that follows, wafer 118, or at least inspection area 120A, is silicone dioxide on a silicon base. It should be understood that FIG. 2A is not to scale and is for purposes of illustration only.

Figure 3C:
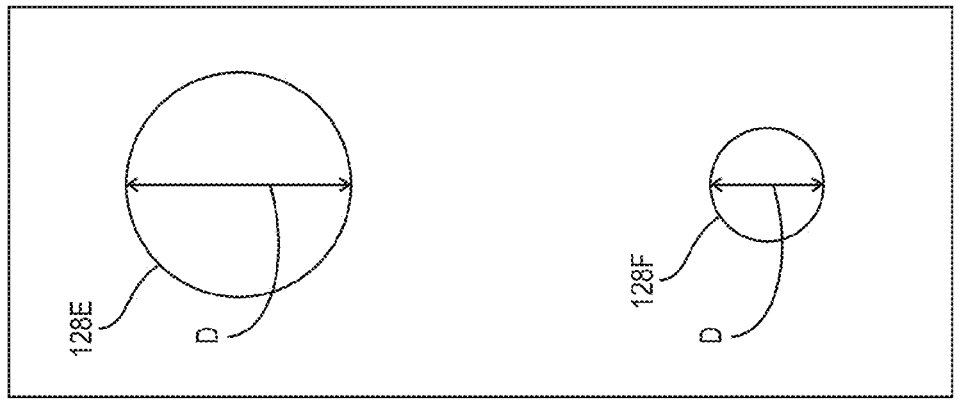
FIGS. 3A through 3C illustrate example image shapes.
Figure 3B:
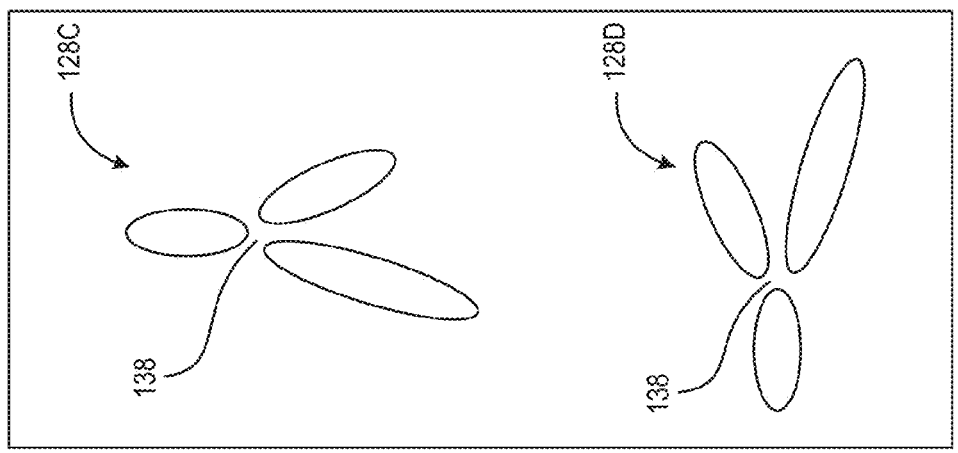
Figure 3A:
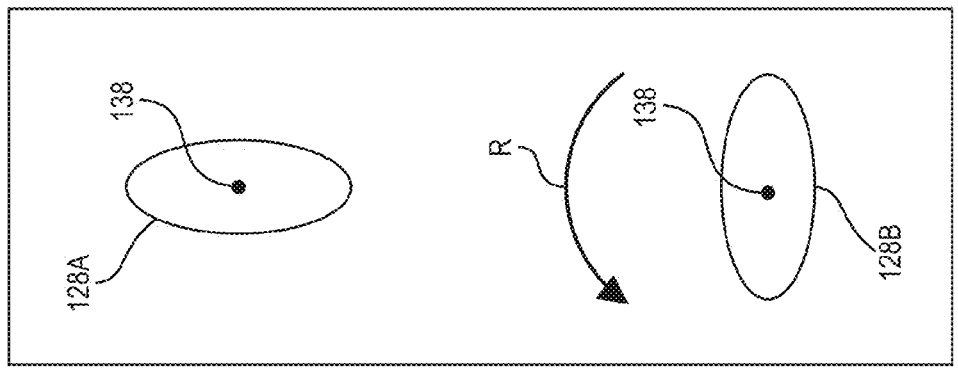

FIGS. 3A through 3C illustrate example image shapes. The following should be viewed in light of FIGS. 1 through 3C. Detector 111 detects light 122 scattered by or reflected from wafer 118 by beam 116 impinging on wafer 118. Detector 111 generates and transmits signal 124 characterizing detected light 122. By "characterize" we mean that the signal describes, or quantifies, light 122, for example, providing parameters enabling generation of an image using the signal. Processor 106 is configured to execute the computer readable instructions to generate, using signal 124, image 126 including at least one shape 128. Shape(s) 128 can be: a single shape, such as ellipses 128 shown in FIG. 3A; multiple lobes 128 as shown in FIG. 3B; or a disc, such as discs 128 shown in FIG. 3C.

Figure 4A:
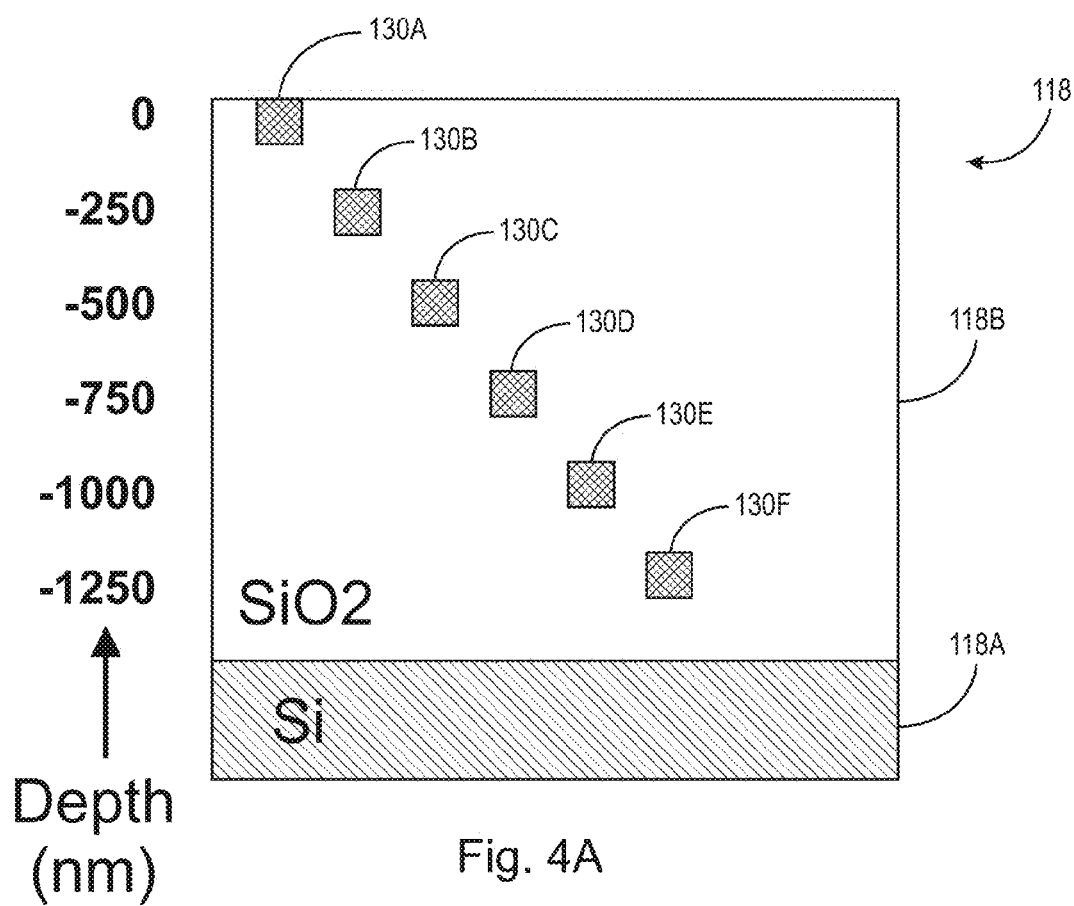
FIG. 4A is a graphical side view of a semi-conductor wafer showing defects in the wafer.

FIG. 4A is a graphical side view of semi-conductor wafer 118 showing defects 130 in the wafer.

Figure 4B:
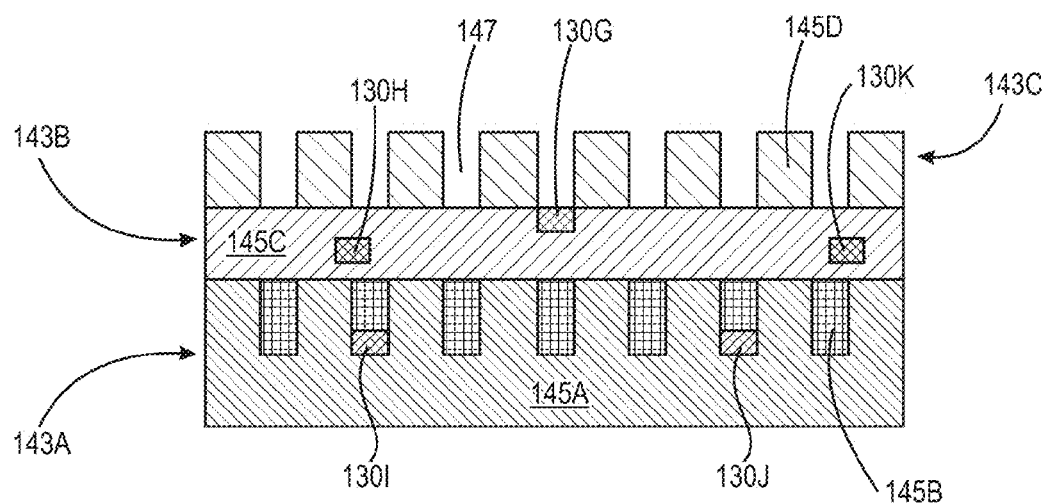
FIG. 4B is a graphical side view of a semi-conductor wafer showing defects in the wafer.

FIG. 4B is a graphical side view of semi-conductor wafer 118 showing defects 130 in the wafer.

Figure 5:
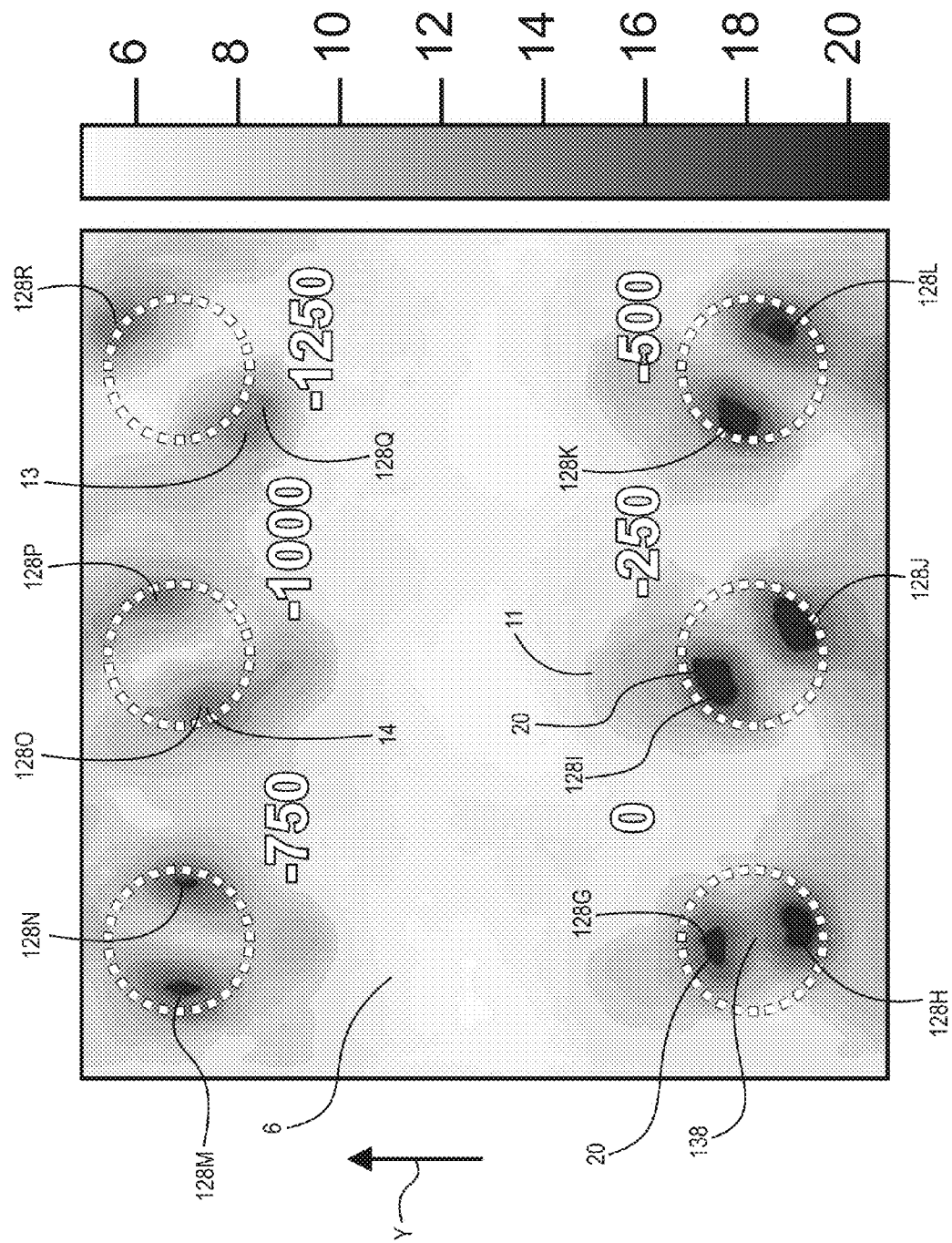
FIG. 5 is pictorial representation of respective lobe pairs associated with defects in a semi-conductor wafer.

FIG. 5 is graphical representation of respective lobe pairs associated with features in a semi-conductor wafer. The following should be viewed in light of FIGS. 1 through 5. Defect 130 can be any defect known in the art that constitutes a defect of interest (DOI) which may adversely impact structure or function of the wafer, or that constitutes a nuisance that can be effectively ignored. For example, a defect is characterized by having a light scatter different from surrounding structure and can be a particle, a gap, or a missing or misshaped pattern. Processor 106 is configured to execute the computer readable instructions to determine orientation 132 of shape(s) 128 or size 134 of shape(s) 128 and to calculate depth 136, in a z direction orthogonal to the x and y directions, of defect 130, as further described below, in the wafer according to orientation 132 or size 134.

In FIGS. 3A, 3B, and 5, determining orientation 132 includes determining respective positions of shape(s) 128 with respect to rotation about a point or points 138 in the image, for example in direction R. Note that direction R can be reversed. As further described below, depth 136 is ascertained from the respective rotational positions. For example, in FIG. 3A, ellipses 128A and 128B have different respective rotational positions with respect to point 138, with ellipse 128A representing a defect at the surface of the wafer and ellipse 128B representing a defect deeper in the wafer. For example, in FIG. 4B, lobe groupings 128C and 128D have different respective rotational positions with respect to point 138, with group 128C representing a defect at the surface of the wafer and group 128D representing a defect deeper in the wafer.

For example, in FIG. 4C, discs 128E and 128F have different respective diameters D. D for disc 128E, representing a defect at the surface of the wafer, is greater than D for disc 128F representing a defect deeper in the wafer. Depth 136 is ascertained from the respective diameters. Note that other size differences and configurations are possible.

In FIG. 5 a color scale of intensities 6 (red—lowest intensity) to 20 (purple—greatest intensity) is shown on the right-hand side. In the example of FIG. 5, pairs of lobes 128, for example, lobes 128G and 128H, have greater intensity than the background and are clearly differentiated from the background. Advantageously, lobes 128 associated with defects nearest surface 120 are particularly well differentiated. In the example of FIG. 5, pairs of lobes 128, for example, lobes 128G and 128H, are substantially diametrically opposed about center point 138. Processor 106 is configured to execute the computer readable instructions to determine the orientation of pairs of lobes 128 by determining a rotation of lobe pairs 128 with respect to points 138 as further described below.

In an example embodiment, the memory element stores point spread function (PSF) 140 and processor 106 is configured to execute the computer readable instructions to generate image 126, in particular shapes 128, using function 140.

In the example of FIG. 4, wafer 118 includes base 118A of silicon and portion 118B of silicon dioxide. The respective depths of defects 130A-F in portion 118B are shown on the left-hand side of the figure. In this example, each defect is assumed to have a respective area in the x-y plane of 124 square nm. Defects 130A-F correspond to lobe pairs 128G/H, 128I/J, 128K/L, 128M/N, 128O/P, and 128Q/R, respectively. As seen in FIG. 5, the rotational orientation of a pair of lobes 128 changes with depth in the wafer. For example, using a horizontal y axis as a reference line, lobes 128G/H are nearly parallel to the y axis. This orientation (along with the intensity of the lobes) indicates that defect 130A is at the surface of the wafer. As the z depth of the features increases, the respective lobes rotate in a counter-clockwise direction. Lobes 128M/N, for defect 130F (having a z depth of 750 nm) are substantially orthogonal to the y axis and lobes 128Q/R, at the greatest depth of 1,250 nm, continue the counter-clockwise rotation. In an example embodiment, the processor uses algorithm or a look-up table 142, stored in memory 104, to determine depth 136 from orientation 132.

FIG. 5 illustrates a case in which wafer 118 a more complicated structure including layers 143A/B/C. Layer 143A is of single material 145A. Layer 143B includes materials 145B/C. Layer 143C includes material 145D. Gaps 147 are between segments of layer 143C. Defects 130G-K are shown. In this example, defect 130G at the surface of layer 143B is a DOI. However, it should be understood that any of the defects in FIG. 5 could be deemed a DOI depending upon the particular conditions involved.

In an example embodiment, apparatus 100 includes optical component groups 144, 146, and 148. Groups 144, 146, and 148 include any optical components known in the art, such as lenses or mirrors, and are used as is known in the art to condition or direct beams 112, 116, and 122, respectively. In an example embodiment, apparatus 100 includes mirror 150.

Figure 6:
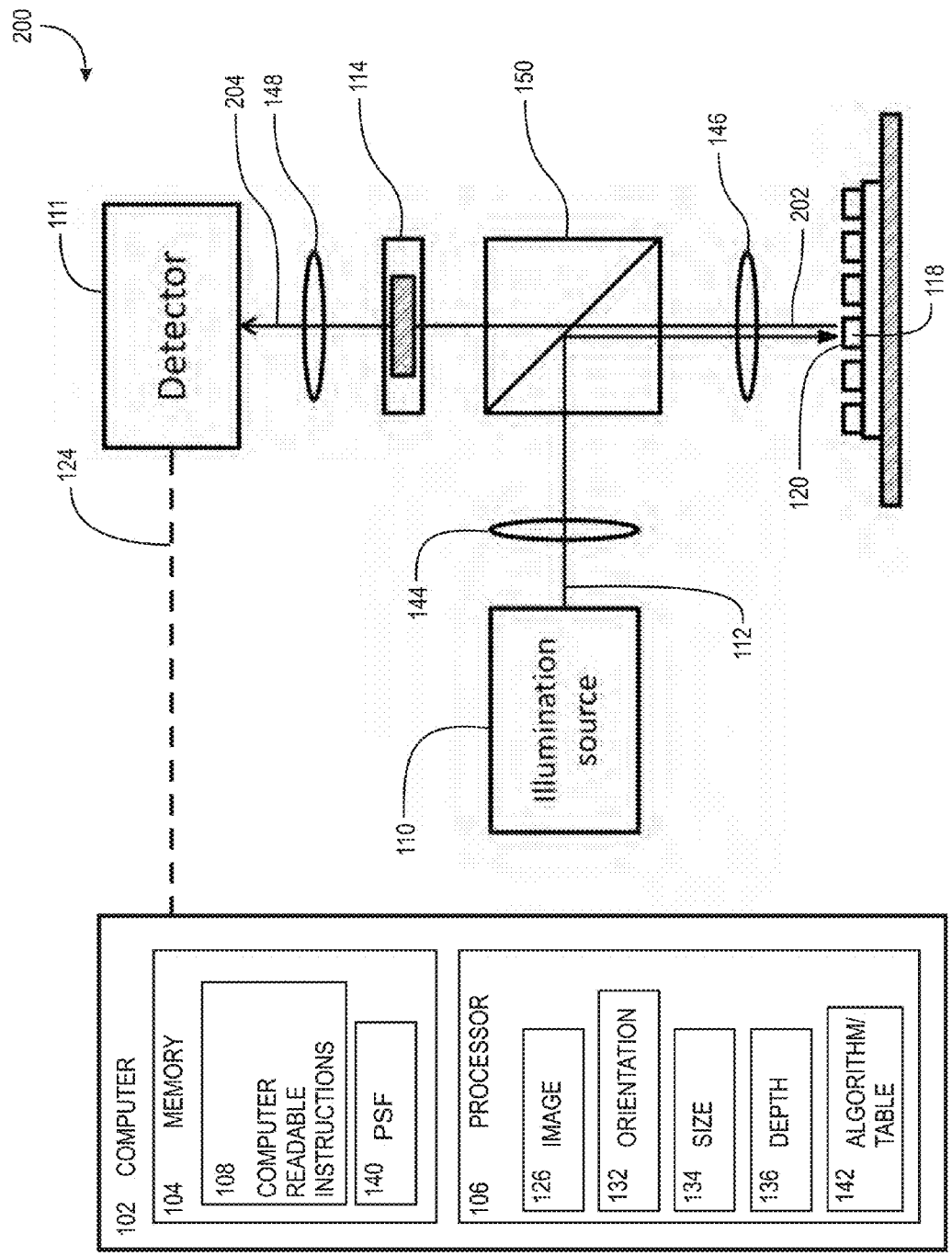
FIG. 6 is schematic representation of a computer-based apparatus for inspecting a semi-conductor wafer using a spiral light beam.

FIG. 6 is schematic block diagram of computer-based apparatus 200 for inspecting a semi-conductor wafer using a spiral light beam. The following should be viewed in light of FIGS. 1 through 6. System 200 includes computer 102, memory element 104, and processor 106. System 200 includes light, or illumination, source 110 and detector 111. Light source 110 is arranged to illuminate wafer 118 with light 112 free of a spiral wavefront or orbital angular momentum. Phase filter 114 is arranged to filter light 202, which is light 112 scattered by or reflected from wafer 118, to generate light beam 204, rotating in a spiral about a central axis (for example as shown in FIG. 1) and having orbital angular velocity. Detector 111 detects beam 204. Detector 111 generates and transmits signal 124 characterizing detected beam 204. Processor 106 is configured to execute the computer readable instructions to generate, using signal 124, image 126. The discussion for FIGS. 2 through 5 regarding image 126, shape or shapes 128, defects 130, orientation 132, size 134, and depth 136 is applicable to FIG. 6.

In an example embodiment, apparatus 200 includes optical component groups 144, 146, and 148. Groups 144, 146, and 148 include any optical components known in the art, such as lenses or mirrors, and are used as is known in the art to condition or direct beams 112, 202, and 204, respectively. In an example embodiment, apparatus 100 includes mirror 150.

The rotation angle of a spiral beam with orbital angular momentum, such as beam 116 or 204 for example, in particular the rapid rotation of the beam, enables the extraction of more accurate z depth information from image 126. For example, the rapid rotation enables more precise correlation of the orientations of shapes 128 to z depths of respective defects 130. For example, a greater span of rotation for shapes 128 for a particular span in the z direction is possible, enabling greater sensitivity of z depth detection and determination. Simply stated, the greater the number of revolutions executed by the spiral light beam in a particular depth range of the wafer, the more accurate the depth information obtainable for that range.

Figure 7:
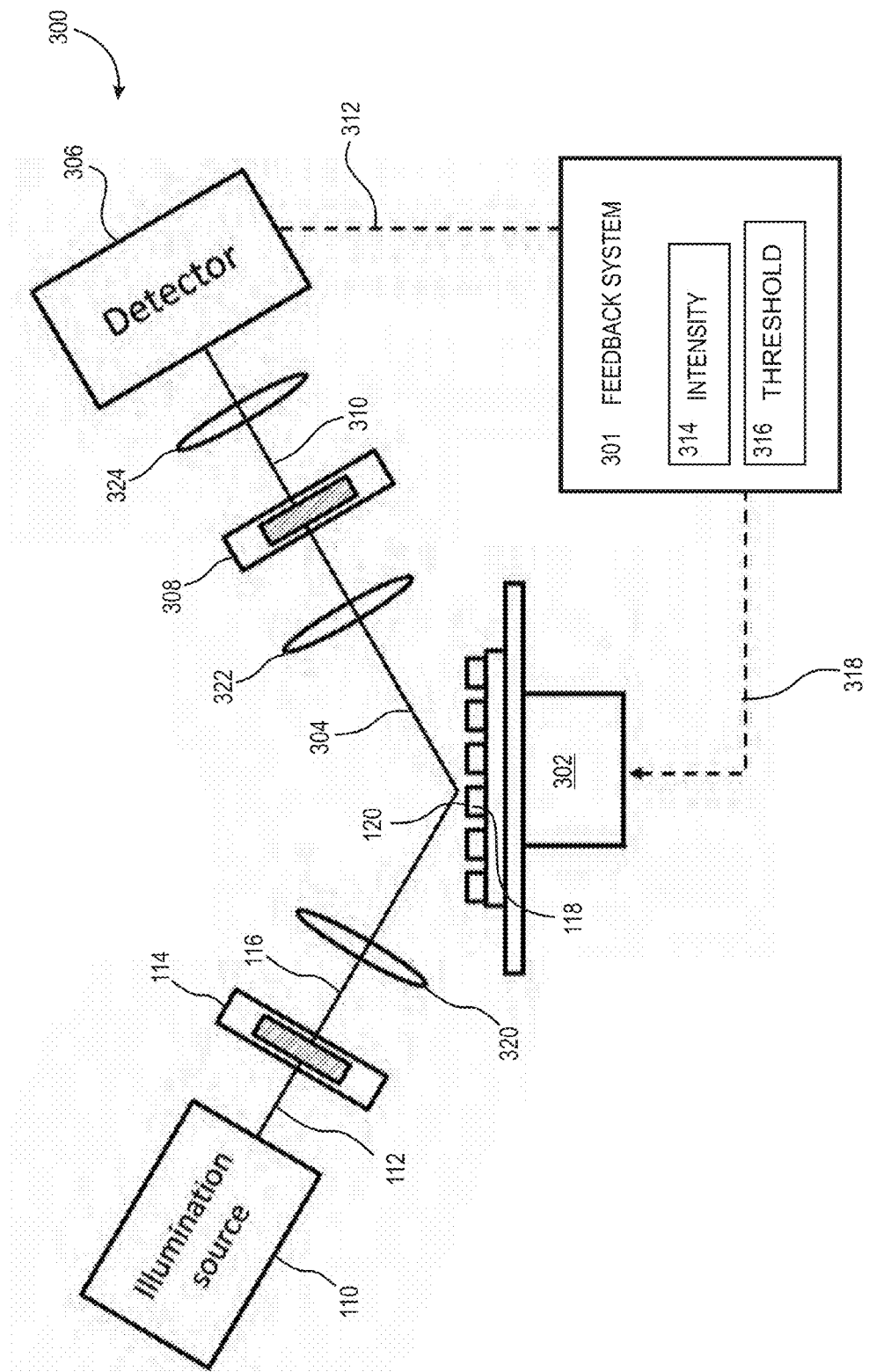
FIG. 7 is schematic representation of a computer-based apparatus for inspecting a semi-conductor wafer using a spiral light beam for auto-focus.

FIG. 7 is schematic representation of computer-based apparatus 300 for inspecting a semi-conductor wafer using a spiral light beam for auto-focus. The purpose of an auto-focus function for apparatus 300 is to place, in the z direction, each wafer 118 to be inspected at a same position. Apparatus 300 includes electronic feedback loop system 301 and wafer adjustment mechanism 302. In an example embodiment computer 102 includes system 301. System 301 can be any electronic feedback system known in the art. Apparatus 300 includes light or illumination source 110 arranged to emit light 112 free of a spiral wavefront or orbital angular momentum. Phase filter 114 is arranged to filter light 112 to generate light beam 116. Light beam 116 illuminates wafer 118. Light beam 304, scattered by or reflected from surface 120 of the wafer, is directed toward detector 306 and is intercepted by filter 308. The rotational configuration of beam 304 is dependent upon the z position of surface 120. Filter 308 is configured to block some or all of beam 304 when surface 120 is not in a desired z position, or to strengthen beam 304 when surface 120 is in the desired z position. Detector 306 detects any light 310, which is the portion of light beam 304 passing through filter 308, and transmits signal 312 to loop 106 regarding light 310. System 301 compares intensity 314 of light 310 (using signal 312) to preselected threshold 316. When intensity 314 is less than preselected threshold 316, the processor transmits signal 318 to adjust, using mechanism 302, a z position of the wafer until intensity 314 matches threshold 316.

In an example embodiment, filter 308 is a blocking filter. For example, if light beam 304 includes a pair of lobes 128, openings in filter 308 are positioned to coincide with a lobe pair 128 in light beam 308 corresponding to the desired position in the z direction. Filter 308 is configured to substantially block lobe pairs in light beam 308 corresponding to positions in the z direction other than the desired position. Thus, intensity 314 equals or exceeds threshold 316 only for lobe pair 128 in light beam 308 corresponding to the desired position in the z direction.

In an example embodiment, filter 308 is a phase filter matched to filter 114 to give rotation in the opposite direction. For example, for pairs of lobes 128, phase filter 308 is configured to recombine lobes for a specific orientation (associated with surface 120 at the desired z position) to create a peak intensity greater than the respective intensities for any other lobe orientation. Thus, intensity 314 equals or exceeds threshold 316 only for lobe pair 128 in light beam 308 corresponding to the desired position in the z direction.

In an example embodiment, apparatus 300 includes optical component groups 320, 322, and 324. Groups 320, 322, and 324 include any optical components known in the art, such as lenses or mirrors, and are used as is known in the art to condition or direct beams 116, 304, and 310.

Figure 8:
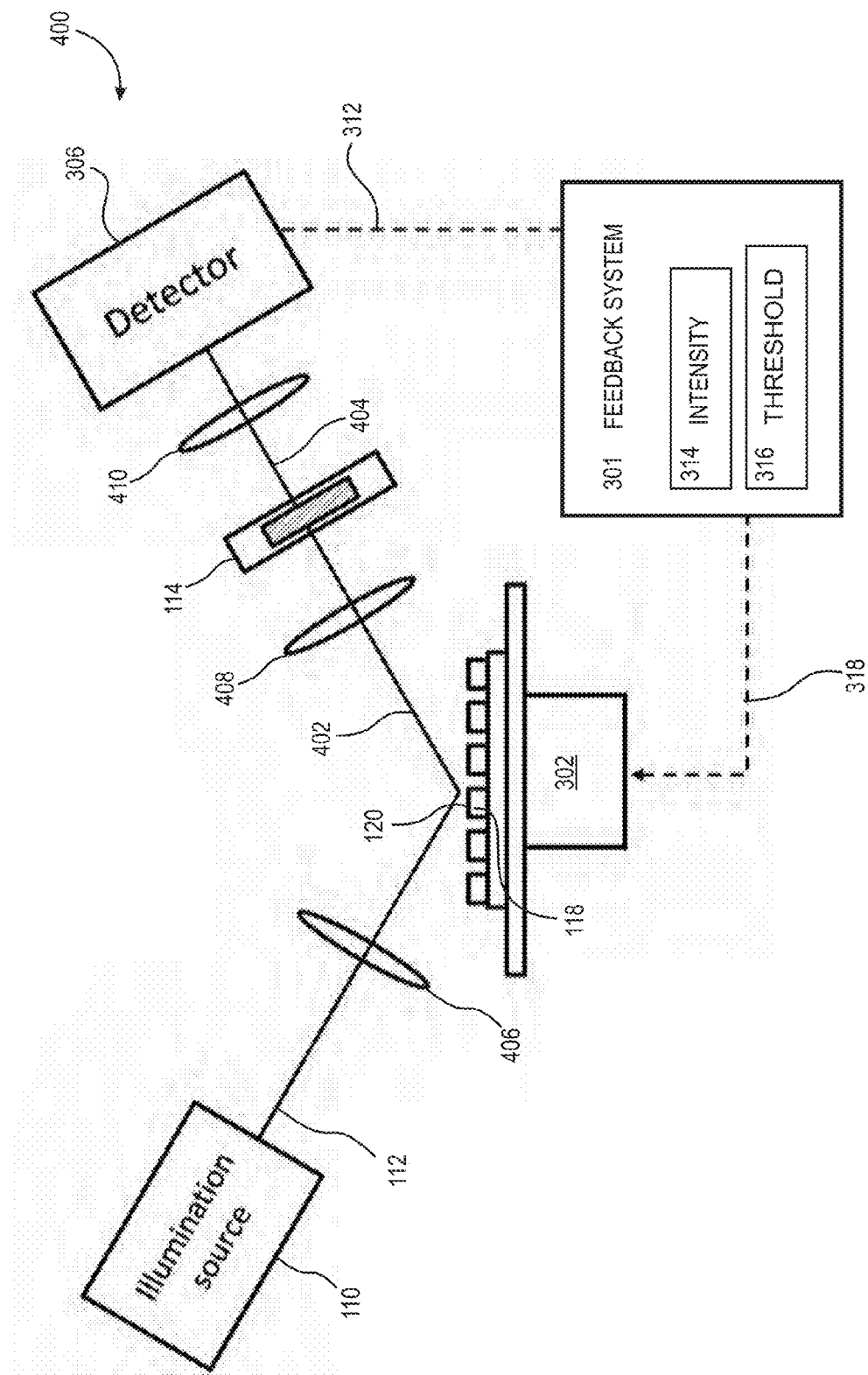
FIG. 8 is schematic representation of a computer-based apparatus for inspecting a semi-conductor wafer using a spiral light beam for auto-focus.

FIG. 8 is schematic representation of computer-based apparatus 400 for inspecting a semi-conductor wafer using a spiral light beam for auto-focus. The purpose of an auto-focus function for apparatus 400 is to place, in the z direction, each wafer 118 to be inspected at a same position. Apparatus 400 includes wafer adjustment mechanism 302, computer 102 with memory element 104 and processor 106. Memory element 104 is configured to store computer readable instructions 108. Apparatus 400 includes light or illumination source 110 arranged to emit light 112 free of a spiral wavefront or orbital angular momentum. Phase filter 114 is arranged to filter light 402, which is light 112 scattered by or reflected from surface 120 of the wafer and directed to detector 306, to generate light beam 404. The rotational configuration of beam 404 is dependent upon the z position of surface 120. Beam 404 includes shape or shapes 128 associated with a z position of surface 120, for example, a pair of lobes 128. The intensity of the lobes is greatest when surface 120 is at the desired z position and this intensity is used as threshold 316. Processor 106 executes instruction 108 to determine, using signal 312, intensity 314 of beam 404. When intensity 314 is less than preselected threshold 316, the processor adjusts, using mechanism 302, a z position of the wafer until intensity 314 matches threshold 316.

In an example embodiment, apparatus 300 includes optical component groups 406, 408, and 410. Groups 406, 408, and 410 include any optical components known in the art, such as lenses or mirrors, and are used as is known in the art to condition or direct beams 112, 402, and 404, respectively.

In an example embodiment, the determination of depth 136 is only implemented for defects 130 (DOIs) at a predetermined position in the z direction. Using FIG. 5 as an example, only defects having corresponding lobes 128 in the configuration of lobes 128G/H (at surface 120) are considered. The configuration of lobes 128 G/H is measured or calculated and used as a kernel for deconvolution of wafer images 126 prior to determining orientation 132 and depth 136. Thus, signal 124 for a DOI is amplified, while signals 124 for other defects are attenuated. Advantageously, signal 124 for a DOI is recovered prior to determining orientation 132 and depth 136, which increases sensitivity and enables more accurate DOI detection.

Figure 9A:
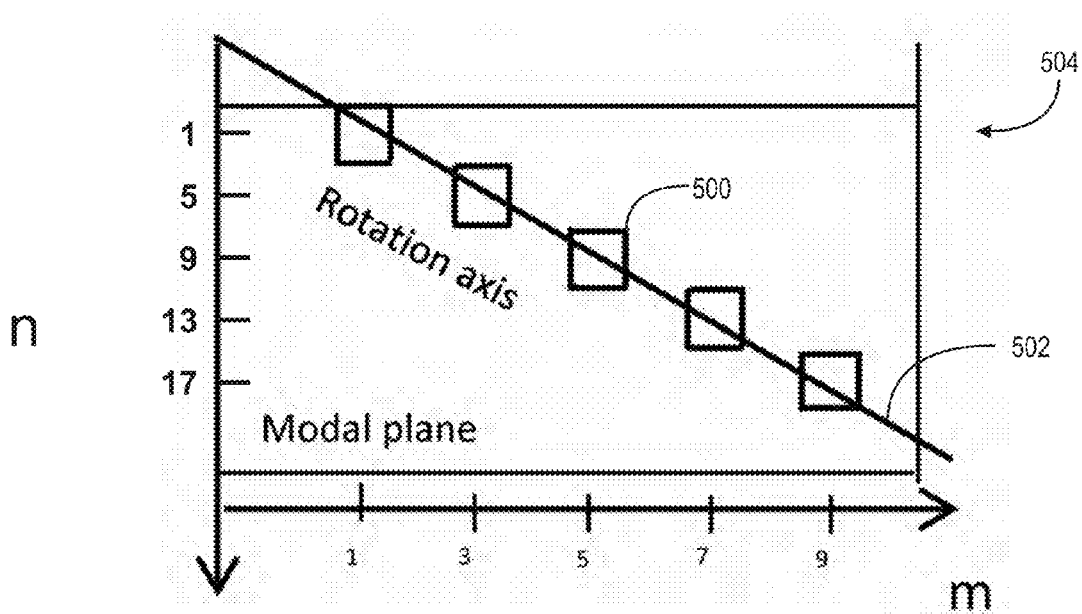
FIG. 9A is a graph showing a plot of Gauss-Laguerre Eigen modes in a modal plane using a known structure for a phase filter.
Figure 9B:
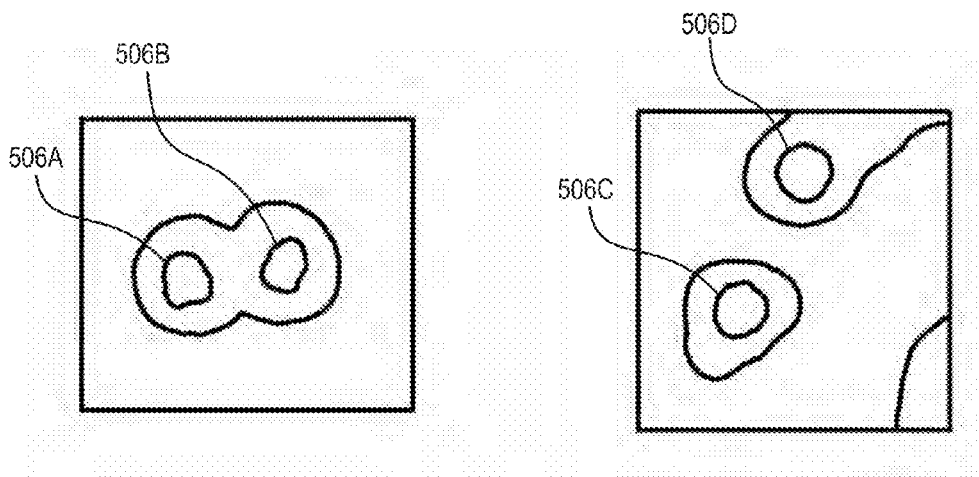
FIG. 9B illustrates example image shapes for defects at a surface of a wafer and at a depth in the wafer.

FIG. 9A is a graph showing a plot of Gauss-Laguerre Eigen modes in a modal plane using a known structure for phase filter 114. FIG. 9B illustrates example image shapes for defects at surface 120 and at a depth of 750 nm in the wafer. Phase filter 114 is uniquely described by a set of Gauss-Laguerre Eigen modes and is based on the interference effect of several Gauss-Laguerre Eigen modes. Gauss-Laguerre Eigen modes are further described in Rafael Piestun, Yoav Y. Schechner and Joseph Shamir, "Propagation-invariant wave fields with finite energy," J. Opt. Soc. Am. A, Vol. 17, No. 2, February 2000, which is incorporated herein in its entirety. The Gauss-Laguerre Eigen modes satisfy two criteria. First, the resulting beam cross-section has the expected non-axially symmetric PSF, for example, double lobes 128 as shown in FIG. 5. Second, the interference pattern of any pair of selected modes gives the same intensity pattern angular rotation speed along the propagation axis.

Each of the Gauss-Laguerre Eigen modes is characterized by two numbers $|n,m\rangle$: n—is the energy number and m—is the azimuthal number. For example the known phase filter of FIG. 9A is described by a set of Eigen modes 500 as $|1,1\rangle + |5,3\rangle + |9,5\rangle + |13,7\rangle + |17,9\rangle$. The Eigen modes sit on line 502 in modal plane (n,m) 504, referred to as a rotation line. The tilt, or slope, of line 502 determines the rotation speed of the spiral light beam generated by filter 114. Modal planes and rotational lines are further described in Sri Rama Prasanna Pavani and Rafael Piestun, "High-efficiency rotating point spread functions", OPTICS EXPRESS, March 200, Vol. 16, No. 5, p. 3489, which is incorporated herein in its entirety. The slope of line 502 is the change of n over the change of m and is no more than 2.0 in FIG. 9A. In FIG. 9B, using the filter described in FIG. 9A, a defect in surface 120 is shown by lobes 506A/B substantially horizontally aligned, and a defect at a depth of 750 nm in wafer 118 is shown by lobes 506C/D which has rotated 60 degrees from lobes 506A/B.

Figure 10:
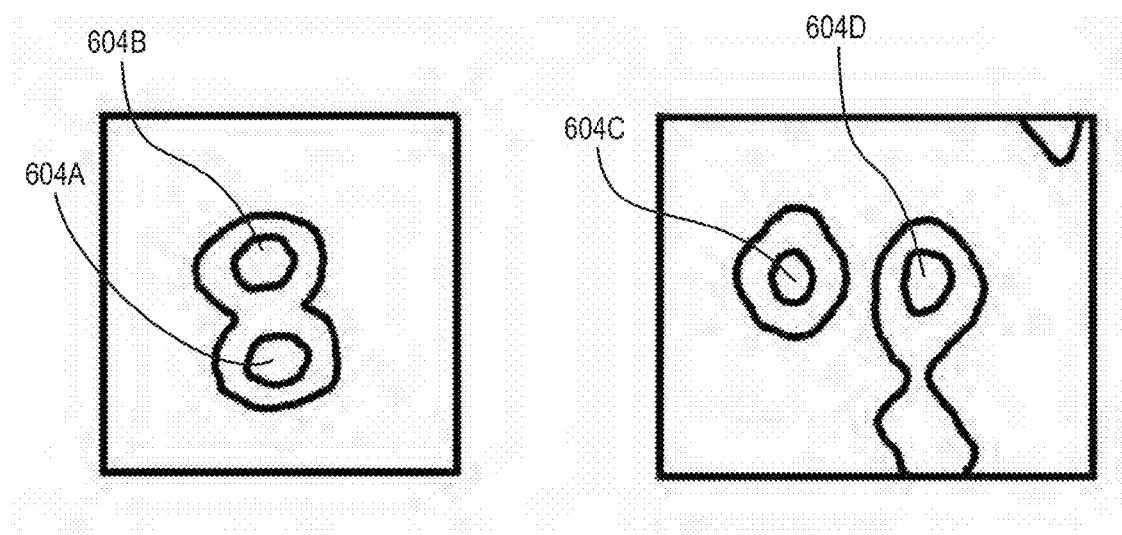
FIG. 10 illustrates example image shapes for defects at a surface of a wafer and at a depth in the wafer.

FIG. 10 illustrates example image shapes for defects at surface 120 and at a depth of 750 nm in the wafer. In an example embodiment, a linear combination of Laguerre polynomials is optimized for filter 114 such that the slope of the rotation line is greater than 2.0. In FIG. 10, using optimized filter 114, a defect in surface 120 is shown by lobes 604A/B substantially vertically aligned, and a defect at a depth of 750 nm in wafer 118 is shown by lobes 604C/D which has rotated 90 degrees from lobes 604A/B.

Figure 11:
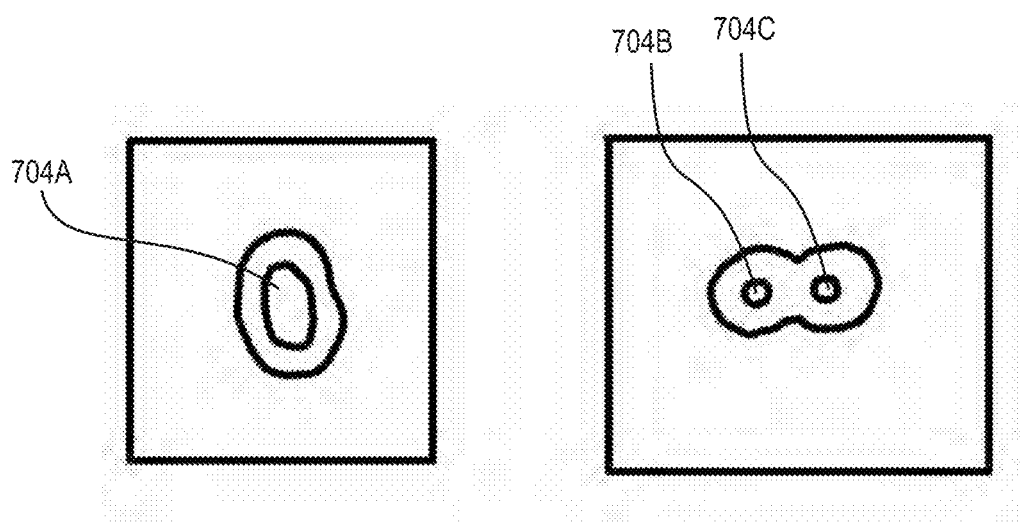
FIG. 11 illustrates example image shapes for defects at a surface of a wafer and at a depth in the wafer; and, FIG. 12 is a pictorial representation of light intensity used in a prior art method for determining a depth of a defect in a semi-conductor wafer.
Figure 12:
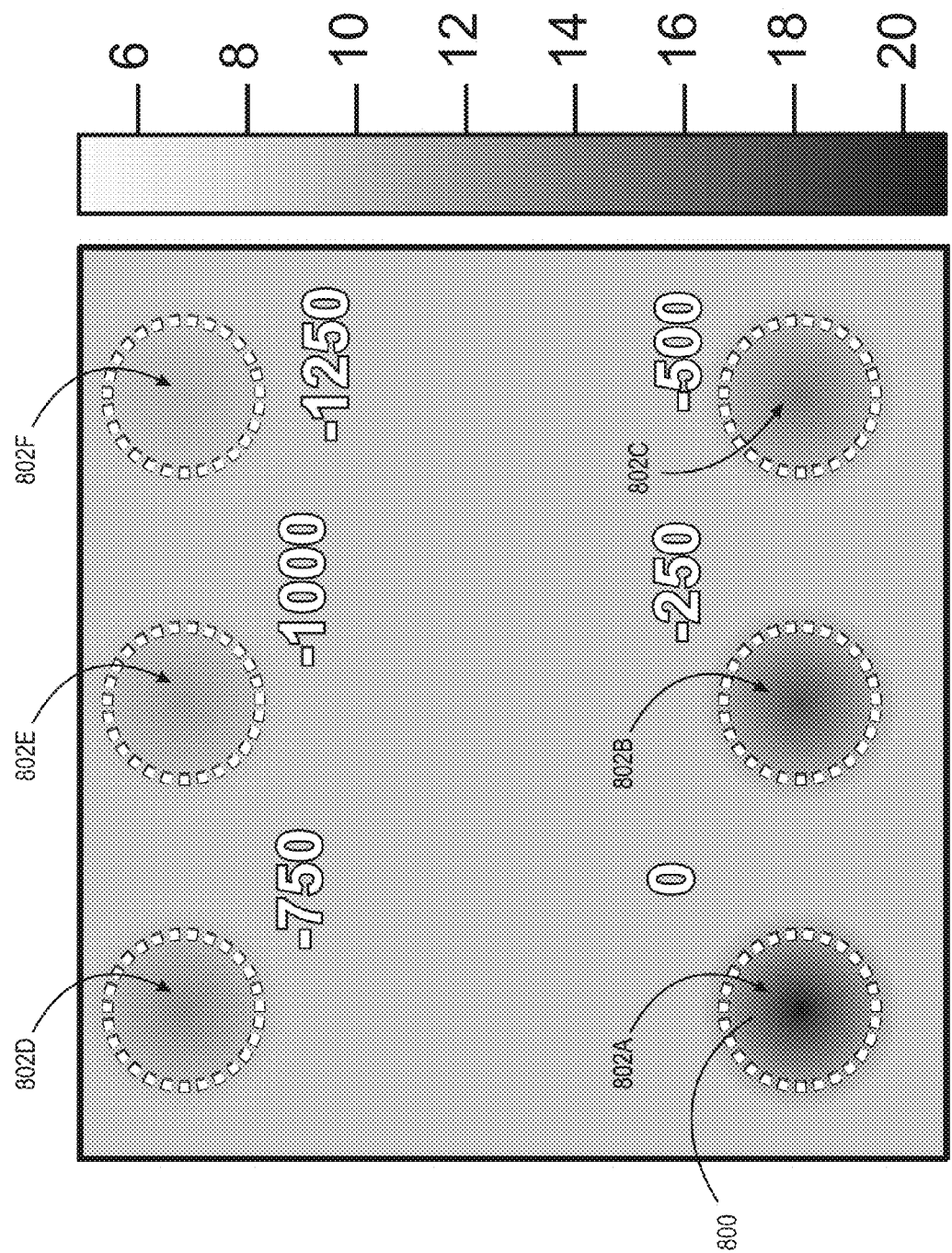

FIG. 11 illustrates example image shapes for defects at surface 120 and at a depth of 750 nm in the wafer. In an example embodiment, a linear combination of Laguerre polynomials is optimized for filter 114 such that the slope of the rotation line is greater than 2.0. In FIG. 10, using optimized filter 114, a defect in surface 120 is shown by lobes 704A/B substantially vertically aligned, and a defect at a depth of 750 nm in wafer 118 is shown by lobes 704C/D which has rotated 90 degrees from lobes 704A/B.

Due to the increased slope of the rotational line, optimized filter 114 generates about 50% faster rotation of a spiral light beam than filter 114 described by FIG. 9A. As noted above, increasing the rotational speed of a spiral light beam increases the accuracy and sensitivity of the determination of defect depth possible using the spiral light beam. For example, in FIGS. 10 and 11, there is an extra 30 degrees of rotation for a depth of 750 nm. Thus, there is an extra 30 degrees with which to express depth variations between surface 120 and a depth of 750 nm. Thus, optimized filter 114 advantageously enables increased accuracy and sensitivity of defect depth determination due to the increased rotation speed imparted by the filters. Advantageously, the increased accuracy and sensitivity enables more accurate discernment of DOIs and nuisance defects.

Energy redistribution into a pair of lobes, such as a pair of lobes 128, by filter 114 can result in lower peak signals of the lobes. Therefore, in an example embodiment, filter 114 is configured to provide further filter profile optimization to improve energy and signal localization inside the pairs of lobes. Higher signals for the lobes improve the capture rate of DOIs by threshold detection methods. Details of filter profile optimization procedure can be found in Sri Rama Prasanna Pavani and Rafael Piestun, "High-efficiency rotating point spread functions", OPTICS EXPRESS, March 200, Vol. 16, No. 5, p. 3489.

The following discussion is directed to apparatus 100; however, it should be understood that the discussion is applicable to apparatus 200, 300, and 400 as well. Advantageously, apparatus 100 enables more sensitive determination of depth position for defects in a semi-conductor wafer (or z position of a surface of the wafer for apparatus 300 and 400). For example, the rapid rotation of beam 116 enables apparatus 100 to discern depth differences of a little as about 200 nm, and for apparatus 300 and 400, enables z positioning of the wafer by increments of about 200 nm. Further, apparatus 100 does not use a focal plane to determine depth of a feature; therefore, apparatus 100 is not subject to the problems noted above for known defect detection systems. Thus, the accuracy of depth determination by apparatus 100 is not dependent upon or influenced by a thickness of the layer being measured. Further, the size or nature of a defect does not impact the orientation of shapes 128 (and subsequent determination of the depth of the defect), overcoming another problem noted above. Apparatus 100 provides accurate result for thinner, planar wafers as well as thick structures such as tri-gate transistors and 3-D NAND memories.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A computer-based method for inspecting a wafer, comprising:
    storing, in a memory element for at least one computer, computer readable instructions;
    detecting, using a detector, a first light beam rotating in a first spiral about a first central axis; and,
    executing, using a processor for the at least one computer, the computer readable instructions to:
    generate, using the detected first light beam, an image including at least one shape;
    determine an orientation of the at least one shape or a size of the at least one shape; and,
    calculate a depth of a defect within the wafer according to the orientation or the size, wherein:
    the at least one shape includes a plurality of shapes; and,
    determining the orientation of the at least one shape includes determining respective positions of the plurality of shapes with respect to rotation about a point in the image.

2. The computer-based method of claim 1, further comprising:
    illuminating, using a light source, the wafer with a second light beam rotating in a second spiral about a second central axis, wherein:
    the first light beam includes the second light beam scattered by or reflected from the wafer.

3. The computer-based method of claim 1, further comprising:
    illuminating, using a light source, the wafer with light free of a spiral wavefront or orbital angular momentum; and,
    filtering, using a phase and transmission filter, the light scattered by or reflected from the wafer to generate the first light beam.

4. The computer-based method of claim 1, wherein:
    the first light beam includes orbital angular momentum.

5. The computer-based method of claim 1, further comprising executing, using the processor, the computer readable instructions to:
    deconvolute, prior to determining the orientation, the image according to a predetermined orientation; or,
    amplify a signal for the at least one shape when the shape matches the predetermined orientation, or attenuate a signal for the at least one shape when the shape does not match the predetermined orientation.

6. A computer-based apparatus for inspecting a wafer, comprising:
    at least one computer including a processor and a memory element configured to store computer readable instructions; and,
    a detector arranged to detect a first light beam rotating in a first spiral about a first central axis, wherein:
    the processor is configured to execute the computer readable instructions to:
    generate, using the detected first light beam, an image including at least one shape;
    determine an orientation of the at least one shape or a size of the at least one shape; and,
    calculate a depth of a defect within the wafer according to the orientation or the size;
    the at least one shape includes a plurality of shapes; and,
    determining the orientation of the at least one shape includes determining respective positions of the plurality of shapes with respect to rotation about a point in the image.

7. The computer-based apparatus of claim 6, further comprising:
    a light source arranged to emit light free of a spiral wavefront or orbital angular momentum; and,
    a phase and transmission filter arranged to filter the light to generate a second light beam, rotating in a second spiral about a second central axis, to illuminate the wafer, wherein:
    the first light beam includes the second light beam scattered by or reflected from the wafer.

8. The computer-based apparatus of claim 5, further comprising:
    a light source arranged to illuminate the wafer with light free of a spiral wavefront or orbital angular momentum; and,
    a phase and transmission filter arranged to filter the light scattered by or reflected from the wafer to generate the first light beam.

9. The computer-based apparatus of claim 6, wherein the processor is configured to execute the computer readable instructions to:
    deconvolute, prior to determining the first orientation, the image according to a predetermined orientation; or,
    amplify a signal for the at least one shape when the shape matches the predetermined orientation, or attenuate a signal for the at least one shape when the shape does not match the predetermined orientation.

10. The computer-based apparatus for inspecting a wafer, of claim 6, wherein:
    the wafer includes a silicon layer and a layer of silicon dioxide overlaying the silicon layer;
    the surface is formed by the silicon dioxide layer; and,
    the surface is not in contact with the silicon layer.

11. A computer-based method for inspecting a wafer, comprising:
- storing, in a memory element for at least one computer, computer readable instructions;
- detecting, using a detector, a first light beam rotating in a first spiral about a first central axis; and,
- executing, using a processor for the at least one computer, the computer readable instructions to:
- generate, using the detected first light beam, an image including at least one shape;
- determine an orientation of the at least one shape or a size of the at least one shape; and,
- calculate a depth, from a surface of the wafer, of a defect within the wafer according to the orientation or the size, wherein:
- the wafer includes a silicon layer and a layer of silicon dioxide overlaying the silicon layer;
- the surface is formed by the silicon dioxide layer;
- the surface is not in contact with the silicon layer;
- the at least one shape includes a plurality of shapes; and,
- determining the orientation of the at least one shape includes determining respective positions of the plurality of shapes with respect to rotation about a point in the image.

12. The computer-based method for inspecting a wafer, of claim 1, wherein the depth is measured from a surface of the wafer.

13. The computer-based method for inspecting a wafer, of claim 1, wherein the defect extends to the surface.

14. The computer-based method for inspecting a wafer, of claim 1, wherein the defect does not extend to the surface.

15. The computer-based method for inspecting a wafer, of claim 1, wherein:
- the wafer includes a silicon layer and a layer of silicon dioxide overlaying the silicon layer;
- the surface is formed by the silicon dioxide layer; and,
- the surface is not in contact with the silicon layer.

16. The computer-based method for inspecting a wafer, of claim 1,
- wherein:
  - the wafer includes a plurality of layers, each layer including a respective material;
  - the defect is within at least one layer included in the plurality of layers; and,
  - the surface is formed by a first layer included in the plurality of layers; and,
- wherein:
  - at least one layer in the plurality of layers includes separate segments of the respective material; or,
  - at least one layer in the plurality of layers includes a second material different from the respective material.

17. The computer-based method for inspecting a wafer, of claim 1, further comprising:
- generating the at least one shape in the at least one image using a phase and transmission filter inserted in the first light beam.

18. The computer-based apparatus of claim 6, wherein the depth is measured from a surface of the wafer.

19. The computer-based apparatus of claim 6, wherein the defect extends to the surface.

20. The computer-based apparatus of claim 6, wherein the defect does not extend to the surface.

21. The computer-based apparatus of claim 6,
- wherein:
  - the wafer includes a plurality of layers, each layer including a respective material;
  - the defect is within at least one layer included in the plurality of layers; and,
  - the surface is formed by a first layer included in the plurality of layers; and,
- wherein:
  - at least one layer in the plurality of layers includes separate segments of the respective material; or,
  - at least one layer in the plurality of layers includes a second material different from the respective material.

22. The computer-based apparatus of claim 6, further comprising:
- a phase and transmission filter inserted in the first light beam, the phase and transmission filter arranged to generate the at least one shape in the at least one image.

23. A computer-based apparatus for inspecting a wafer, comprising:
- at least one computer including a processor and a memory element configured to store computer readable instructions; and,
- a detector arranged to detect a first light beam rotating in a first spiral about a first central axis, wherein:
- the processor is configured to execute the computer readable instructions to:
- generate, using the detected first light beam, an image including at least one shape;
- determine an orientation of the at least one shape or a size of the at least one shape; and,
- calculate a depth of a defect within the wafer according to the orientation or the size, wherein:
- the wafer includes:
  - a plurality of layers, each layer including a respective material;
  - at least one layer in the plurality of layers includes:
    - separate segments of the respective material; or,
    - separate segments of a second material different from the respective material;
- the surface is formed by a first layer included in the plurality of layers;
- the defect is within at least one layer included in the plurality of layers;
- the at least one shape includes a plurality of shapes; and,
- determining the orientation of the at least one shape includes determining respective positions of the plurality of shapes with respect to rotation about a point in the image.

* * * * *